US008231542B2

(12) United States Patent
Keith et al.

(10) Patent No.: US 8,231,542 B2
(45) Date of Patent: *Jul. 31, 2012

(54) SYSTEM FOR ANALYZING THERMAL DATA BASED ON BREAST SURFACE TEMPERATURE TO DETERMINE SUSPECT CONDITIONS

(75) Inventors: Louis G. Keith, Chicago, IL (US); William H. Reeves, Cedar Lake, IN (US); Jimmy D. Holmes, Reno, NV (US); Rajendra Acharya U, Singapore (SG); Ng Yin Kwee, Singapore (SG)

(73) Assignee: Lifeline Biotechnologies, Inc., Reno, NV (US)

( * ) Notice: Subject to any disclaimer, the term of this patent is extended or adjusted under 35 U.S.C. 154(b) by 385 days.

This patent is subject to a terminal disclaimer.

(21) Appl. No.: 12/583,969

(22) Filed: Aug. 27, 2009

(65) Prior Publication Data
US 2010/0056946 A1 Mar. 4, 2010

Related U.S. Application Data

(63) Continuation-in-part of application No. 12/198,967, filed on Aug. 27, 2008, now Pat. No. 8,185,485.

(51) Int. Cl.
*A61B 5/00* (2006.01)
(52) U.S. Cl. ....................................................... 600/549
(58) Field of Classification Search .................. 600/549
See application file for complete search history.

(56) References Cited

U.S. PATENT DOCUMENTS

| 3,877,463 | A | 4/1975 | Cary et al. |
| 3,995,621 | A | 12/1976 | Fletcher et al. |
| 5,301,681 | A | 4/1994 | DeBan et al. |
| 5,810,010 | A | 9/1998 | Anbar |
| 5,820,263 | A | 10/1998 | Ciobanu |
| 5,941,832 | A | 8/1999 | Tumey et al. |
| 5,961,466 | A | 10/1999 | Anbar |
| 5,999,843 | A | 12/1999 | Anbar |
| 6,023,637 | A | 2/2000 | Liu et al. |
| 6,067,371 | A | 5/2000 | Gouge et al. |
| 6,389,305 | B1 * | 5/2002 | Deban et al. ................. 600/427 |
| 2004/0002663 | A1 | 1/2004 | Reeves |
| 2007/0213617 | A1 | 9/2007 | Berman et al. |
| 2008/0004904 | A1 | 1/2008 | Tran |

OTHER PUBLICATIONS

Gulzer et al. "Bi-modal breast cancer classification system" 2004 p. 235-242.*
Land "Breast Cancer Computer aided diagnosis using a recently developed SVM/GRNN oracle Hybrid" IEEE 2003, pp. 1-3.*

(Continued)

*Primary Examiner* — Max Hindenburg
*Assistant Examiner* — Renee Danega
(74) *Attorney, Agent, or Firm* — Woodcock Washburn LLP

(57) ABSTRACT

A portable computing device or microprocessor/storage system including temperature sensors used to collect temperature readings of a breast tissue of a subject. The device would collect data from the sensors at regular time intervals over a period of time. All of the generated temperature data is stored in the portable computing or storage device. The sensors are placed on the greatest areas of interest on the breast, based on where most cancers develop, by using a sensor placeholder. The sensor placeholder would be lobate shaped, with the sensor placeholder aligning with the glandular regions of the breast where cancers are most likely to develop. The temperature data is then analyzed by one or more classifier systems and classified as either suspect or non-suspect tissue.

43 Claims, 9 Drawing Sheets

OTHER PUBLICATIONS

Szu, H.; Kopriva, 1.; Hoekstra, P.; Diakides, N.; Diakides, M.; Buss, J.; Lupo, J.;, "Early tumor detection by multiple infrared unsupervised neural nets fusion," Engineering in Medicine and Biology Society, 2003. Proceedings of the 25th AnnualInternational Conference of the IEEE, vol. 2, no., pp. 1133-1136 vol. 2, Sep. 17-21, 2003.

Koay, J.; Herry, C.; Frize, M.;, "Analysis of breast thermography with an artificial neural network," Engineering in Medicine and Biology Society, 2004. IEMBS '04. 26th Annual International Conference of the IEEE, vol. 1, no., pp. 1159-1162, Sep. 1-5, 2004.

* cited by examiner

SYSTEM FOR ANALYZING THERMAL DATA BASED ON BREAST SURFACE TEMPERATURE TO DETERMINE SUSPECT CONDITIONS

CROSS-REFERENCES TO RELATED APPLICATIONS

This application is a continuation-in-part and claims priority to U.S. patent application Ser. No. 12/198,967, filed Aug. 27, 2008 and incorporated herein by reference.

BRIEF DESCRIPTION OF THE INVENTION

A system for collecting temperature readings of breast tissue of a subject over a period of time based on a set of predetermined positions around the breast and analyzing those temperature readings through one or more classifier systems to classify the breast tissue as either suspect or non-suspect tissue.

STATEMENTS AS TO THE RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

Breast cancer continues to be the second leading cause of death for women between the ages of 40 to 55 in America. The number of women developing breast cancer has increased tremendously from 1:20 in 1960 to 1:7 today. Epidemiological studies estimate that one in eight women will develop breast cancer during their lifetimes. Moreover, one in five women with breast cancer will die of the disease despite the considerable advances in treatment. According to the American Cancer Society, in 2007, an estimated 178,480 new cases and 40,460 deaths from breast cancer in women are expected to occur in the United States. Breast cancer development in men is also increasing. Given these circumstances, early detection of breast cancer is considered an important prognostic factor. Ideally, death from malignancy rather than its lack of detection should be the point of reference in evaluating any screening program.

Breast cancer occurs when cells in the breast begin to grow out of control and invade nearby tissues or spread throughout the body. It is one of the leading causes of cancer death in women. Mammography is the most commonly used screening modality for the early detection of breast cancer. However, mammography is of limited value in young and pre-menopausal women because denser breast tissue produces mammographic images which are difficult if not impossible to interpret. Therefore, there is a need to develop novel and more effective screening strategies with a high sensitivity and specificity.

Cancer development in tissue below the breast surface appears to generate an increase in the temperature on the breast surface. For several decades medical researchers around the world have struggled to find an accurate method for interpreting thermal circadian data related to tumor growth in the breast, and using this as a detection modality. It is recognized that the breast exhibits a circadian rhythm that is reflective of its physiology. Areas of mammalian tissue adjacent to carcinomas exhibit increased temperatures from that exhibited by non-adjacent, non-cancerous areas. The temperature of a cancer-affected area can fluctuate several degrees Centigrade from normal tissue; this difference having been demonstrated while monitoring such an area for a 24-hour period. The relationship between breast skin temperature and breast cancer has been documented and it has been found that the differences between the characteristics of rhythmic changes in skin temperature of clinically healthy and cancerous breasts were real and measurable.

Currently mammography is considered the gold standard as a screening tool for the early detection of breast cancer. Unfortunately, wide variations exist in its sensitivity and specificity in published reports. Mammographic sensitivity varied from 100% in fatty breasts to 4% in extremely dense breasts, as evidenced by a recent study. As a consequence, other technologies have been used in an effort to complement mammography. Magnetic resonance imaging (MRI) has been shown to be more sensitive in the early detection of occult breast cancers, particularly in pre-menopausal women for whom the sensitivity of mammography is compromised, but with less specificity and greater cost. Additional modalities are still under development, such as electrical impedance scanning (EIS), mammary ductoscopy (MD), and proteomics of nipple aspirate fluid (NAF) and serum. In spite of these advances, women in the United States are subjected to numerous unnecessary breast biopsies each year because of the inadequacies of the aforementioned breast cancer detection modalities' inability to separate benign from cancerous lesions.

Recent reports indicate that MRI is able to detect cancer in the contralateral breast even when such cancers were missed by mammography or in clinical examination at the time of the initial breast examination. In addition, MRI has been proven to be a better screening tool for women with genetic mutations of the BRCA1 or BRCA2 genes, and in those women with a strong family history of breast cancer. Although the sensitivity of MRI is better than that of mammography, the technique is flawed by a lower specificity and a far greater expense. However, recently, the American Cancer Society announced a change in its breast cancer screening recommendation guidelines, recommending that women with high genetic risk (such as those who have mutation in the BRCA1 or BRCA2 genes or those with a strong family history of breast cancer) be screened with magnetic resonance imaging.

An additional source of concern relates to the fact that radiologists fail to detect cancer in up to thirty percent of patients with breast cancer despite the fact that the malignancies missed by the radiologists are evident in two thirds of the mammograms. There is a need to further assist radiologists, surgeons and other physicians in detecting, diagnosing, successfully biopsing, and operating on precancerous and cancerous conditions.

The establishment and growth of most tumors depends on the successful recruitment of new blood vessels into and around the tumor cells. This process, also known as angiogenesis, is dependent on the production of angiogenic growth factors by the tumor cells. Angiogenesis results in a more constant blood flow to the area of the tumor, which increases the local temperature in the area surrounding the tumor in comparison to normal breast tissue.

The superficial thermal patterns measured on the surface of the breast are related to tissue metabolism and can serve as a means to visualize activity within the underlying tissue. Such thermal patterns change significantly as a result of normal phenomena including the menstrual cycle, pregnancy and, more importantly, the pathologic process itself. Cancer development, in most instances, represents the summation of a large number of mutations that occur over years, each with its own particular histologic phenotype that can be seen in premenopausal mastectomy specimens. Cancer development appears to generate its own thermal signatures, and the complexity or lack thereof may be a reflection of its degree of development.

Thermographic technology was originally introduced to complement mammography because it was felt that a thermogram of the breast was able to detect breast cancer development up to 10 years earlier than most conventional modalities. However, the accuracy of thermography has remained questionable due to a number of factors, such as the symmetry and stability of the breasts' temperature during the menstrual cycle and temperature fluctuations caused by the use of oral contraception.

One prior device used for detecting cancer is a brassiere that includes a plurality of temperature sensors, an analog multiplexer circuit, a control circuit, a sample and hold circuit, an analog/digital converter, a buffer register, a storage register, a clock and a data logger. The device allows for the storage of temperature readings in a digital form. This digital data may be uploaded to the data logger which converts the digital signals to decimal form so that the temperature differences may be read and analyzed by a supervising physician and the problems associated with such devices are stated in commonly owned U.S. Pat. No. 6,389,305.

Other devices use a passive thermographic analytical apparatus that provide a direct readout of the results through analysis of a thermographic radiation pattern of the human body. Such devices are unable to detect small tumors on the order of less than 0.5 cm and possibly other larger tumors and certain types of cancers, and do not take into account the chaotic fluctuation of normal body temperatures over time and between locations on the body.

Many cancers are diagnosed too late; successful treatment is more attainable if the cancer is found at early stages. Other devices described in U.S. Pat. Nos. 6,389,305, 5,941,832 and 5,301,681 have met with some limited success, but are yet to provide an optimal breast cancer detection device. There remains a need to improve the method and device for detection of potentially cancerous conditions in breasts.

DETAILED DESCRIPTION OF THE INVENTION

Figure 1A:
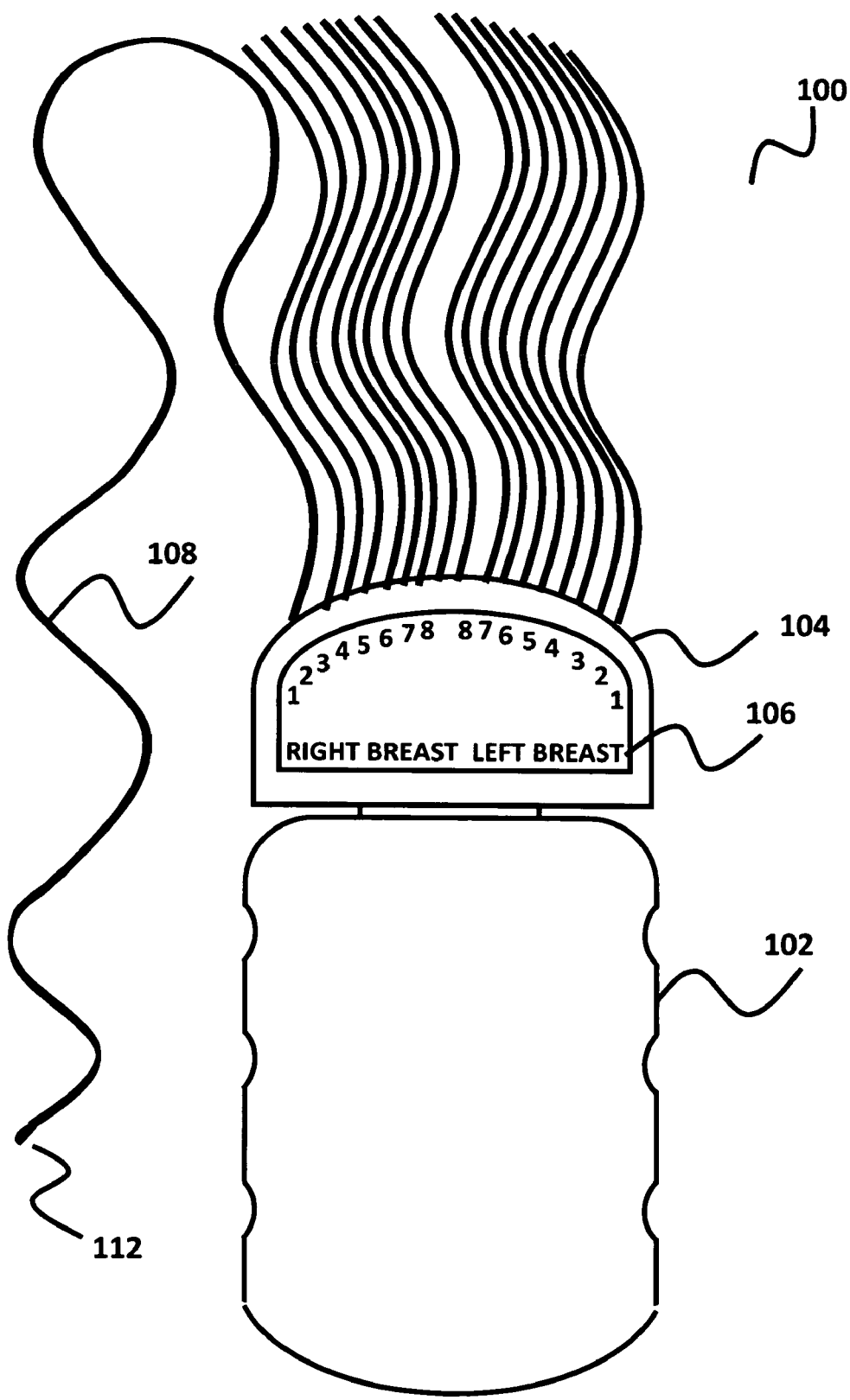
FIG. 1A illustrates a front-view of the preferred embodiment of the present invention.

The present invention is directed to a device and method for providing improved classification of breast tissue as either suspect tissue or non-suspect tissue. Suspect tissue can then be further analyzed using a variety of well-known diagnostic techniques. The device of the present invention includes a set of temperature sensors placed on the left and right breasts of a patient in accordance with a predefined pattern. The sensors collect temperature readings over a predetermined period of time. The collected temperature readings are then classified using one or more classifier systems.

The concept behind the present invention is that new blood vessels supplying a breast cancer do not respond to normal physiological control mechanisms (vasoconstriction and vasodilatation). Therefore, suspect tissue, such as cancers produce time-related pattern changes not seen in normal tissue. These pattern changes have been detected over a circadian (24 hour) rhythm, but can be detected over shorter periods of time, as little as three hours. The present invention views these chaotic changes in the circadian rhythm, or shorter time periods, as a signal of high risk for breast cancer in a tested subject even in the absence of other mammographic evidence, such as an x-ray.

A classifier system is an algorithm that assigns a class label to an object or set of data based on the description and characteristics of the objects or the set of data. A classifier system accepts data as one or more inputs, and outputs the best possible action based on the characteristics of the input data. A classifier system is first trained using a set of data. This allows the classifier system to learn a set of characteristics about the data. For example, an above average temperature in the breasts could signify the presence of cancerous tissue.

A classifier system could be trained using supervised learning, unsupervised learning, reinforcement learning, or a combination of these learning methods. In supervised learning, the training data consists of a set of one or more inputs and a set of expected or desired outputs associated with each input. In unsupervised learning the inputs consists of unlabeled data and the goal is to determine how the data are organized. A form of unsupervised learning is clustering. In reinforcement learning the goal is to maximize some notion of long-term reward in response to a set of one or more inputs. In the preferred embodiment of the present invention, the classifier systems would be trained using supervised learning. Nevertheless, the classifier systems could be trained using other methods including unsupervised learning or reinforcement learning.

The training data could consist of temperature readings with above average temperatures, enabling the classifier system to learn to associate above average temperatures with suspect or cancerous tissue. In addition, the training data could consist of examples of non-cancerous patients in the form of average temperature readings. Additional training data could consist of anomalous temperature readings that change over the test period. For example, a contusion may have an elevated temperature for an initial period of time, but cool off as the contusion heals, or a sensor may loose contact with the skin of the subject for a period to time and indicate a lower than average temperature during that period, or a subject may touch a sensor during a temperature reading causing a higher than average reading for a single reading. This training data would enable the classifier system to learn to associate average temperature readings and temperature readings that decrease over time with non-cancerous tissue.

The output of the classifier system could vary depending on the number of classes needed. For example, if the only two classes of interest are cancerous and non-cancerous, then the output of the classifier system could be a single number, with a value of 0 denoting cancerous tissue and a value of 1 denoting non-cancerous tissue. If the data needed to be further classified as easy to detect or hard to detect, then another number could be output by the classifier system, with 0 denoting easy to detect and 1 denoting hard to detect. Under such a system, for example, an output of two zeros could signify cancerous tissue that is easy to detect.

There are many classifier systems that could be used and that are well known in the art. Further, methods used for the design, training, and testing of classifier systems are numerous. Thus, it is not possible, realistic or necessary to attempt to explain all of those methods in this description. Moreover, it is not necessary to describe such methods herein because anyone of skill in the art of the present invention will be able to implement such functionality without undue experimentation. Nevertheless, a number of different types of classifier systems will be described below.

Once the classifier system reaches a desirable level of performance through training, by correctly displaying the correct output given known input data, the classifier is then tested against a second set of data. The testing against this other set of data is done to check how well the classifier system performs on data it has not been exposed to during training, hence its ability to learn characteristics from the training data.

In the preferred embodiment of the present invention, a neural network would be used as the classifier system. The neural network could be trained using a variety of methods, such as with back-propagation or neuroevolution. There are many supervised and unsupervised learning techniques for neural networks known in the art.

In an alternative embodiment, an ensemble of classifier systems would be used for classification of the temperature data. The ensemble of classifier systems could consist of the same type of classifier system or consist of different types of classifier systems. For example, an ensemble of neural networks could be used to classify the temperature data of a subject, with each neural network from the ensemble having been initialized with different node weights, or each neural network having a different topology, or each neural network using different activation functions, or each network having been trained using a different set of training data. Alternatively, the ensemble could consist of different types of classifiers, such as having one feed-forward neural network, one recurrent neural network, one decision tree, and one support vector machine. When using an ensemble of classifier systems, the output of each classifier system could be handled in different ways to present a diagnosis based on the temperature data. In an embodiment, the most frequent diagnosis from the ensemble of classifier systems is given as the final diagnosis. Alternatively, a weight could be associated with different classifier systems, with the output of each classifier system then given a contribution to the final diagnosis relative to its weight value.

In yet another embodiment, a single classifier system is selected from a group comprising of a neural network, a radial basis function, a Gaussian mixture model, a fuzzy network, and a support vector machine. In an embodiment, a user could pick the specific type of classifier system to use for the classification diagnosis. In another embodiment, all of the classifier systems would be used for the classification diagnosis. Because the performance of the various classifier systems may vary, the diagnosis received by a majority of the classifier systems would then be used as the classification diagnosis. Alternatively, a probability for a certain diagnosis could be presented by taking the number of cancerous or suspect diagnosis divided by the total number of diagnosis. For example, if two out of five classifiers gave a suspect diagnosis, then the system could present the user with a message that states that the user has a 20% chance of currently having cancer or needing consultation to identify the reason for the suspect diagnosis. In yet another embodiment, the specific classifier system to use could be determined based on the subject's demographic and medical information. For example, if the subject is post-menopausal, then a support vector machine could be used as the classifier system. If the subject is under 30 years old, then a neural network could be used instead.

The present invention collects data from a plurality of temperature sensors affixed to the breasts of a subject. The sensors collect temperature data from surrounding tissue of the breasts at regular time intervals, such as every five minutes, over a period of time, such as between three and 24 hours. All of the generated temperature data is stored in a portable computing or storage device. The heads of the sensors are placed on a sensor placeholder, a sensor placeholder being placed on each breast, if both breasts are being tested. In the preferred embodiment of the present invention the portable computing device would consist of a microprocessor and storage unit attached to 16 thermal sensors. In a presently preferred embodiment, the thermal sensors are manufactured by YELLOW SPRINGS INSTRUMENT COMPANY. The microprocessor and storage unit would be manufactured by LIFELINE BIOTECHNOLOGIES.

An alternative portable computing device or a storage system could be used, as long as a suitable interface is provided for receiving the temperature readings from the thermal sensors and subsequently recording and storing these in the storage system or in the portable computing device. For example, the sensors could be connected to a wireless transmitter that transmits the temperature readings as they are taken to a remote storage system, for subsequent analysis, or directly to an analysis system for real-time processing. The portable computing device could also include a clip that would allow for the device to be attached to clothing during the data collection period.

In the preferred embodiment, the patient would wear the portable computing device with the sensors for a total of 24 hours. However, the time period could also be varied, such as 12 hours, six hours, etc. The portable computing device would collect data from the sensors every five minutes, but this time interval could be increased or decreased depending on the patient's medical history, the need for more data, or other medical factors. Once the data collection period ends, the data stored in the portable computing device would be transferred to a computer, where the user would then be able to do the classification analysis with the classifier systems using a desktop application. Alternatively, the data could be uploaded to a website, and the classification analysis could be done over a web interface. If the portable computing device was wirelessly enabled or with a physical wire, such as an Ethernet cable, then the user could directly upload the data to a website or other remote server from the portable computing device, where it could be accessed later for classifier analysis. In yet another embodiment, the portable computing device would include a display, and the subject would be able to run the thermal data analysis on the portable computing device and view the results on the display.

In the preferred embodiment of the present invention, a total of 16 sensors would be used to collect temperature measurements of the breasts, eight sensors placed on the right breast and eight sensors placed on the left breast. The sensors would consist of thermistors, whose use as temperature sensors is well known in the art. Throughout the remainder of this detailed description, the terms 1L-8L will be used to refer to one or more of the sensors or thermistors on the left breast, while the terms 1R-8R will be used to refer to one or more of the sensors or thermistors on the right breast.

FIG. 1A illustrates a front view of the preferred embodiment of the portable device or microprocessor/storage system 100, the system including temperature sensors used to collect temperature readings of the breast tissue of the subject. The body 102 of the system 100 would hold the microprocessor or storage system. The system 100 would include a detachable head 104, the detachable head 104 holding the sensor leads or wires 108 and including an interface to connect with the system body 102. Each sensor wire 108 would include a thermistor or temperature sensor 112 at the end of the wire 108. The sensor wire 108 would be color coded, with each of the eight sensor wires 108 on the right color coded the same as the corresponding eight sensor wires 108 on the left. For example, sensor wire 1L and sensor wire 1R would be coded the same color, 2L and 2R would be coded a different color, etc. The detachable head 104 would include a label 106, with the label specifying the numbering of each sensor 112 for the right breast and the numbering of each sensor 112 for the left breast.

Figure 1B:
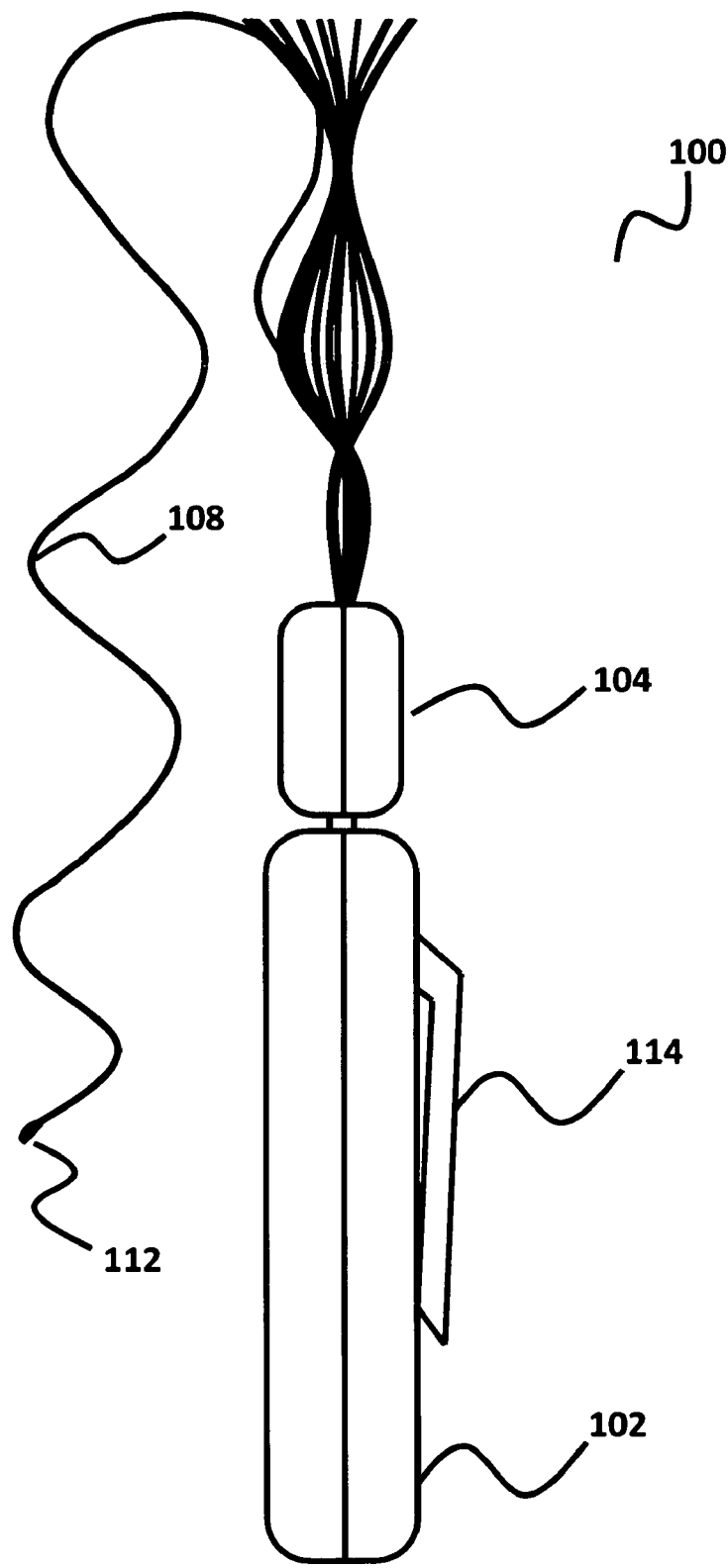
FIG. 1B illustrates a side view of the preferred embodiment of the present invention.
Figure 1C:
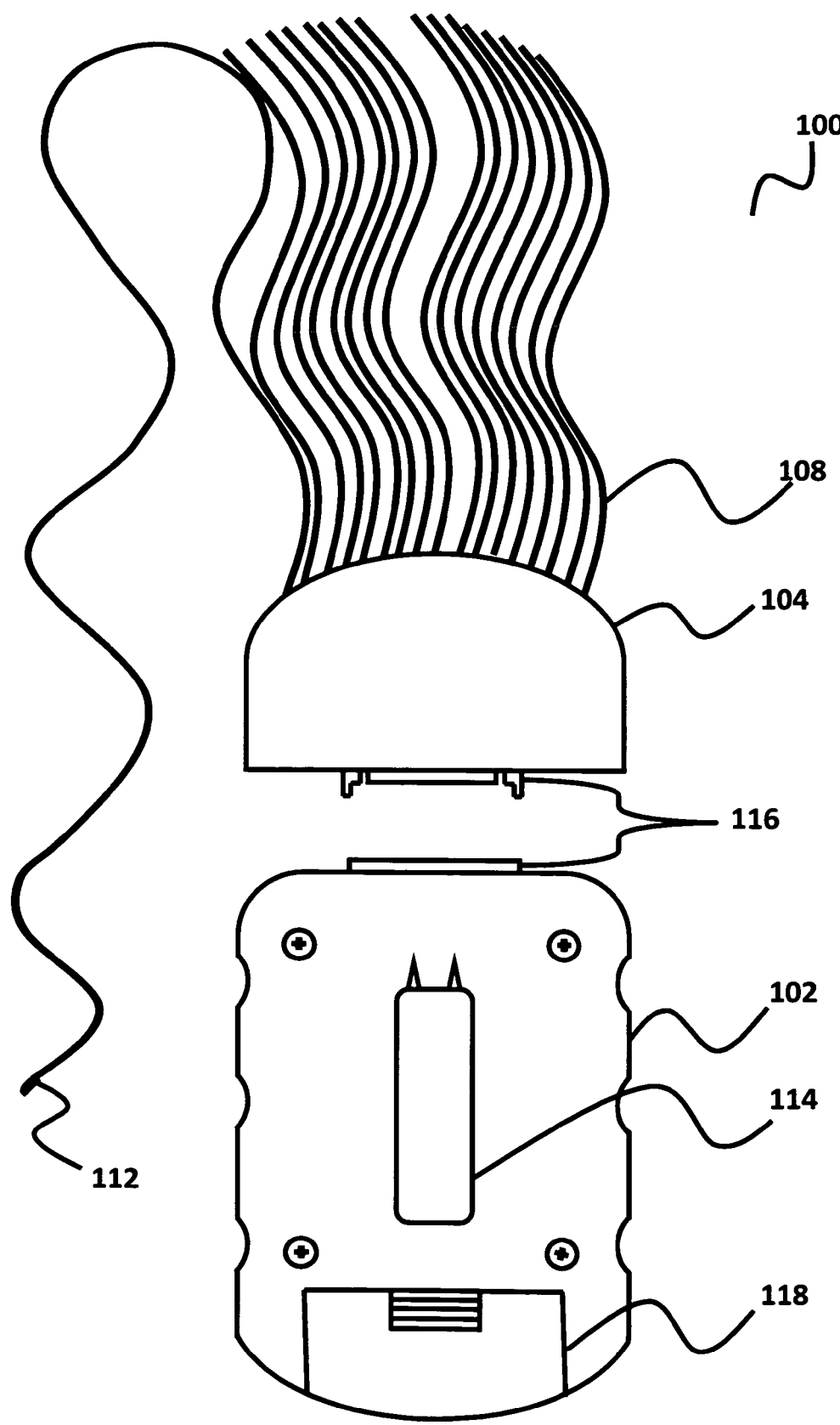
FIG. 1C illustrates a back view of the preferred embodiment of the present invention.

FIG. 1B illustrates a side view of the system 100. The system 100 could include a clip 114 enabling the device to be attached to clothing. FIG. 1C illustrates a back view of the system 100. The hardware interface 116 would be located between the detachable head 104 and the body 102. The type of hardware interface 116 could vary depending on the type of microcontroller used in the body 102 or based on the type of system 100 used. The system would be powered by a battery, housed under the removable cover 118.

Figure 2:
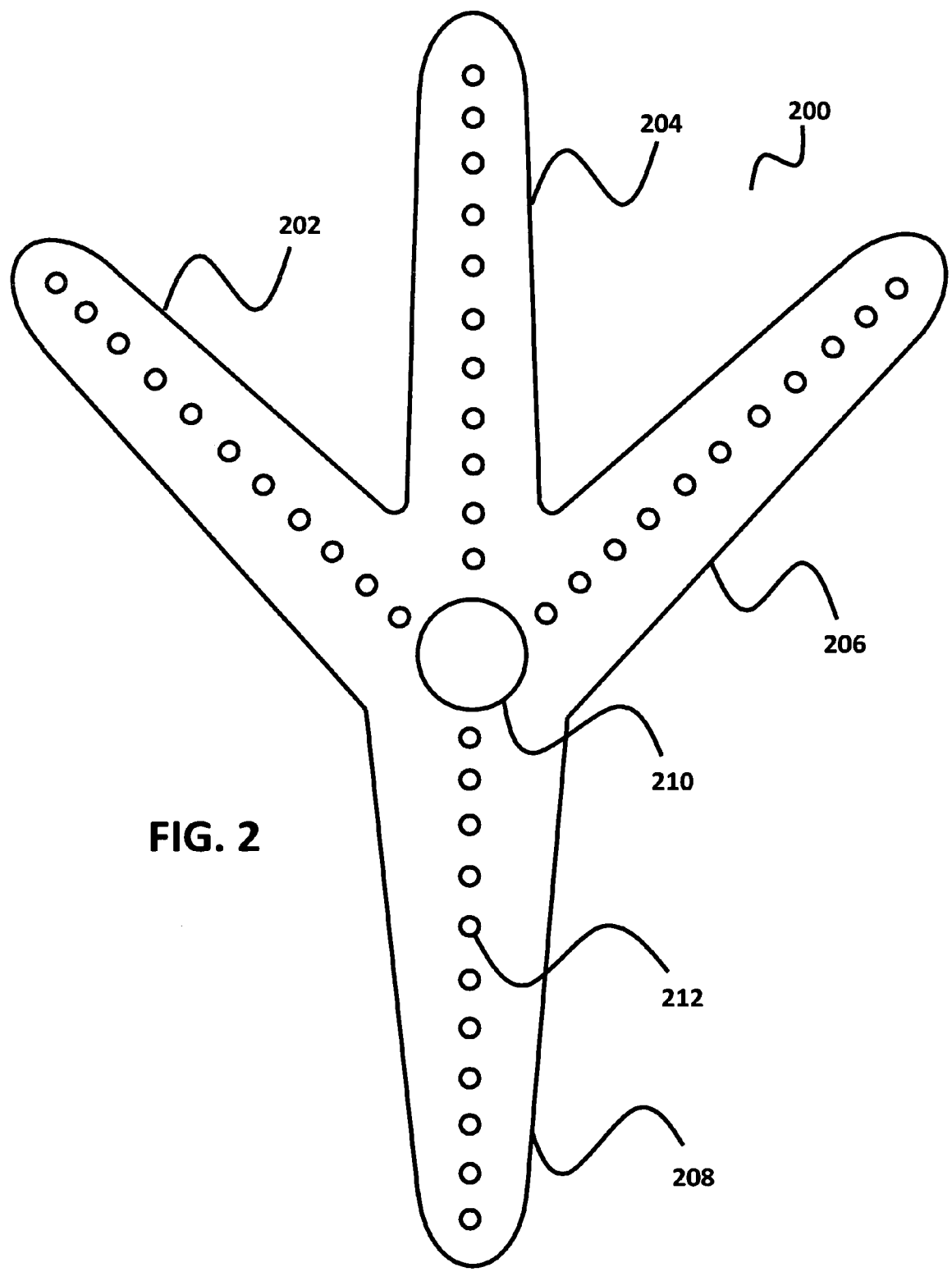
FIG. 2 illustrates the sensor placeholder in accordance with the preferred embodiment of the present invention.

In the preferred embodiment of the present invention, the sensors 112 are placed on the greatest areas of interest on the breast, based on where most breast cancers develop. A sensor placeholder 200, illustrated in FIG. 2, is utilized to facilitate the correct positioning of the sensors on the breast of the subject. The sensor placeholder 200 is preferably lobate shaped with a set of four appendages 202, 204, 206, and 208. Although different shapes could be utilized, as long as such shapes facilitated the placement of sensors on the areas of the breast most prone to cancer, the lobate shape of the sensor placeholder 200 is preferred because it aligns with the glandular regions of the breasts where cancers are most likely to develop and insures proper sensor placement. Each appendage of placeholder 200 preferably includes 11 small holes 212 covering the length of each appendage and ending near the center hole 210, although a different number of holes could be utilized. The center hole 210 of the sensor placeholder 200 would be placed over the nipple of the subject to align the sensor placeholder 200.

Figure 3:
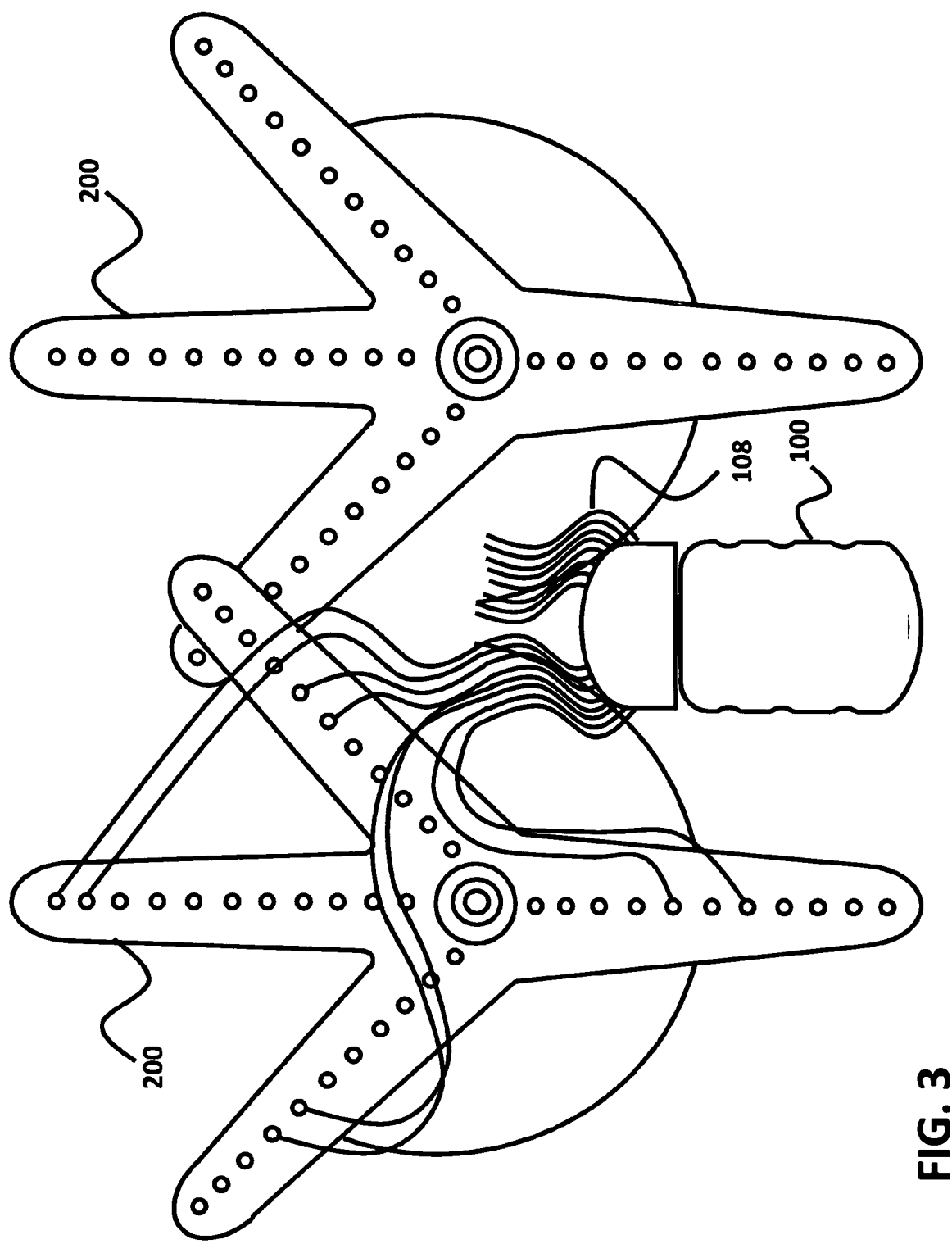
FIG. 3 illustrates a sensor placeholder positioned over the left breast and a second sensor placeholder positioned over the right breast, with the sensors placed over the sensor placeholder.

A sensor placeholder 200 would be placed on each breast as illustrated by the partially broken depiction of FIG. 3. The temperature sensors 112 would be placed in different holes 212 formed by each of the appendages 202, 204, 206, and 208 of the two sensor placeholders 200. The location of the temperature sensors 112 on each of the appendages, and the number of sensors to put on each appendage, will depend on the size of the breast, and any other medical information, such as patient age, status of menopause, the results of previous breast examinations, etc. FIG. 3 illustrates two sensor placeholders 200 placed over the breasts of a subject, with two sensors 112 placed on each appendage of the sensor placeholder position over the right breast of the subject. The positioning of the sensors 112 in FIG. 3 is merely illustrative and does not designate preferred locations for the sensors 112, which are further discussed with reference to FIG. 4 below. Although not shown in FIG. 3, which presents the wires 108 for the left breast as partially broken, the sensors 112 would also be placed in similar locations on the sensor placeholder positioned over the subject's left breast.

Figure 4:
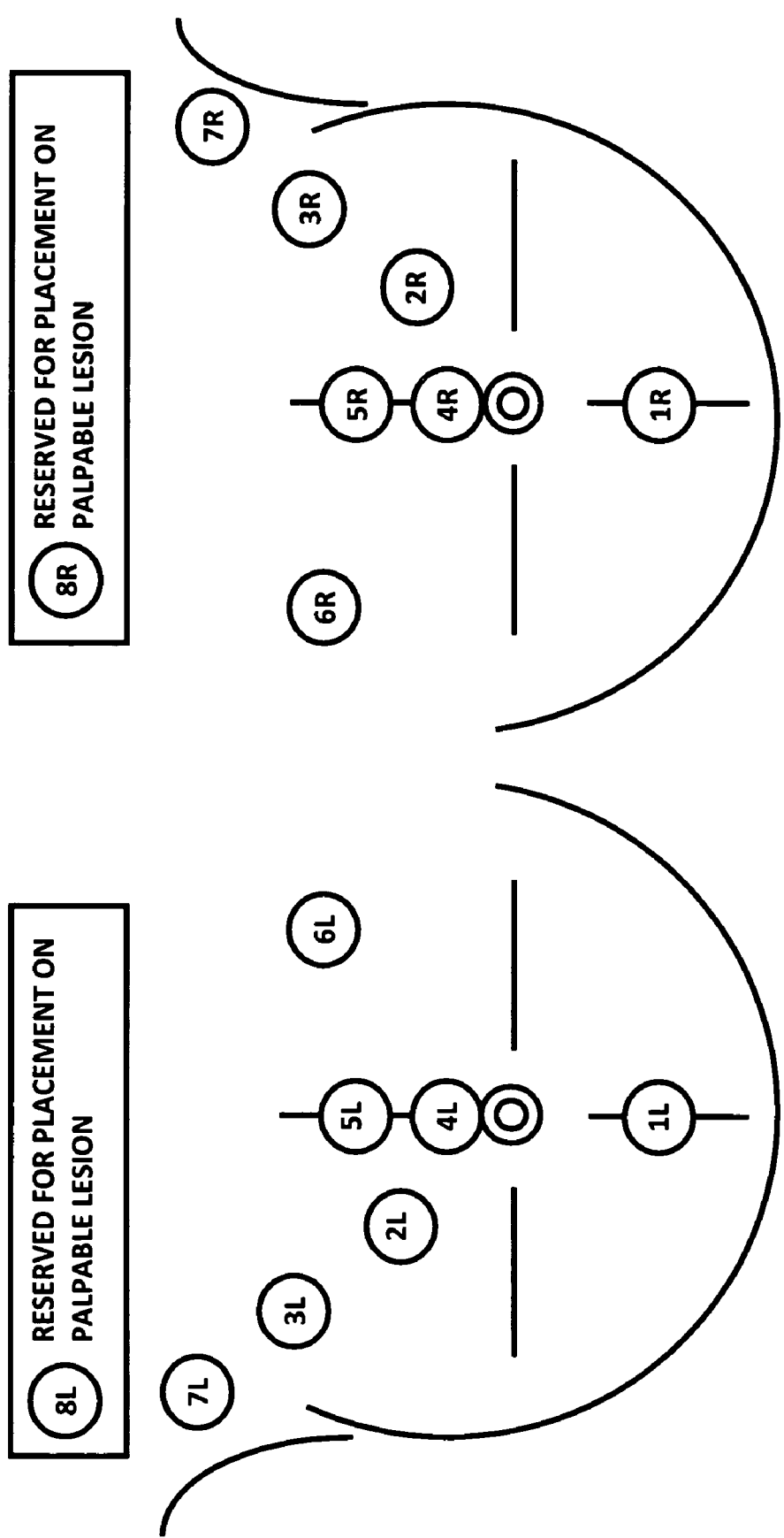
FIG. 4 illustrates the relative positioning of the thermal sensors on the left and right breasts of a subject in accordance with the preferred embodiment of the present invention.

FIG. 4 illustrates the relative positioning of the sensors on the breasts of a subject, based on the most likely occurrence of cancers, in accordance with the preferred embodiment. The thermistors 1L-8L and 1R-8R would be placed on the breasts as follows: 1L and 1R below the nipple; 2L and 2R in the upper outer quadrant; 3L and 3R in the upper outer quadrant toward the axilla; 4L and 4R on the upper areola; 5L and 5R on the vertical midline above the horizontal midline; 6L and 6R in the upper inner quadrant; 7L in an ambient temperature zone; 7R on the sternum; 8L and 8R in a flexible position, such as an area of concern, near the position of a palpable lesion, or at contralateral positions. Each pair of the thermistors (such as 1L/1R, 2L/2R, etc.) is preferably marked to allow for easy identification of each thermistor pair as well as each thermistor. For example, as noted above, each thermistor pair could be color coded and tabbed with a number and letter. Each thermistor and its signals are consequently identified with a specific position on the breast.

The labeling of the data generated by each thermistor simplifies subsequent processing and improves accuracy of the signals in terms of individual signal correlation with calibration data and selection of specific signal sources for manipulation in developing the generalization of physiological condition. This also simplifies correlation of results with specific sensor positions on the breast to arrive at a more specific determination of the location of abnormal physiological conditions. While the number of thermistors and positioning are specifically set forth, it is conceived that accuracy increases as the number of thermistors increases. The eight sensors placed on each breast would be placed in the areas of the breast where the greatest number of breast cancers form, as generally illustrated in FIG. 4.

In the preferred embodiment of the present invention, the temperature readings for the patient would be normalized to a common range, such as the range of 0 to 1. These temperature readings would then be analyzed by the classifier systems. The temperature readings would serve as the input to the classifier systems, and the output of the classifier systems would be a signal or number signifying either a suspect or non-suspect result. While generally a suspect result would be a cancerous one, elevated temperature readings could be due to a number of factors. Many times, the output of the classifier will be such that a very reasonable determination regarding the presence of cancer can be made, but at others, it may be more difficult, so before a potential cancer determination is made, additional testing of suspect tissue may be required.

Normalization of the temperature readings allows for easy comparison of the temperature readings from one or more users. The result of normalization is a data set within the same range, typically from 0 to 1, but any data set can be normalized to any other data range. For example, the data could also be normalized to a number from 0 to 100. Normalization of the temperature data is done by taking each temperature reading and dividing it by the maximum temperature reading in the temperature data. This will result in all numbers being in the range between 0 and 1. Once all numbers have been converted to the 0 to 1 range, they can be further converted to other number ranges as necessary, such as 0 to 100, −100 to 100, 25 to 50, etc. For example, if the maximum temperature reading in all of the collected temperature data for all users is 38 Celsius, then the temperature reading of a particular subject of 32 Celsius would be equal to 32 divided by 38, which is equal to 0.842. If the temperature reading of the particular subject had been equal to 38 Celsius, then the normalized temperature reading would have been equal to 1. Normalization methods are well known in the art.

Outliers in the temperature readings would represent abnormal temperature readings. For example, a subject may be touching a sensor 112 at the time a temperature reading is obtained, or driving in a car with the sun shining on the subject's left breast, but not the right breast. Either of these situations may result in one or more temperature readings that are abnormally high and outside of the range of temperature readings that were taken in the absence of such abnormal circumstances. Such abnormalities can be identified by measuring the difference between any two temperature readings from the sensors at a point in time. Fluctuations in the temperature readings are expected, but any fluctuations beyond a threshold value would be flagged as abnormal readings. Outliers or other anomalous temperature readings would preferably be filtered out by the classifier system.

Figure 5:
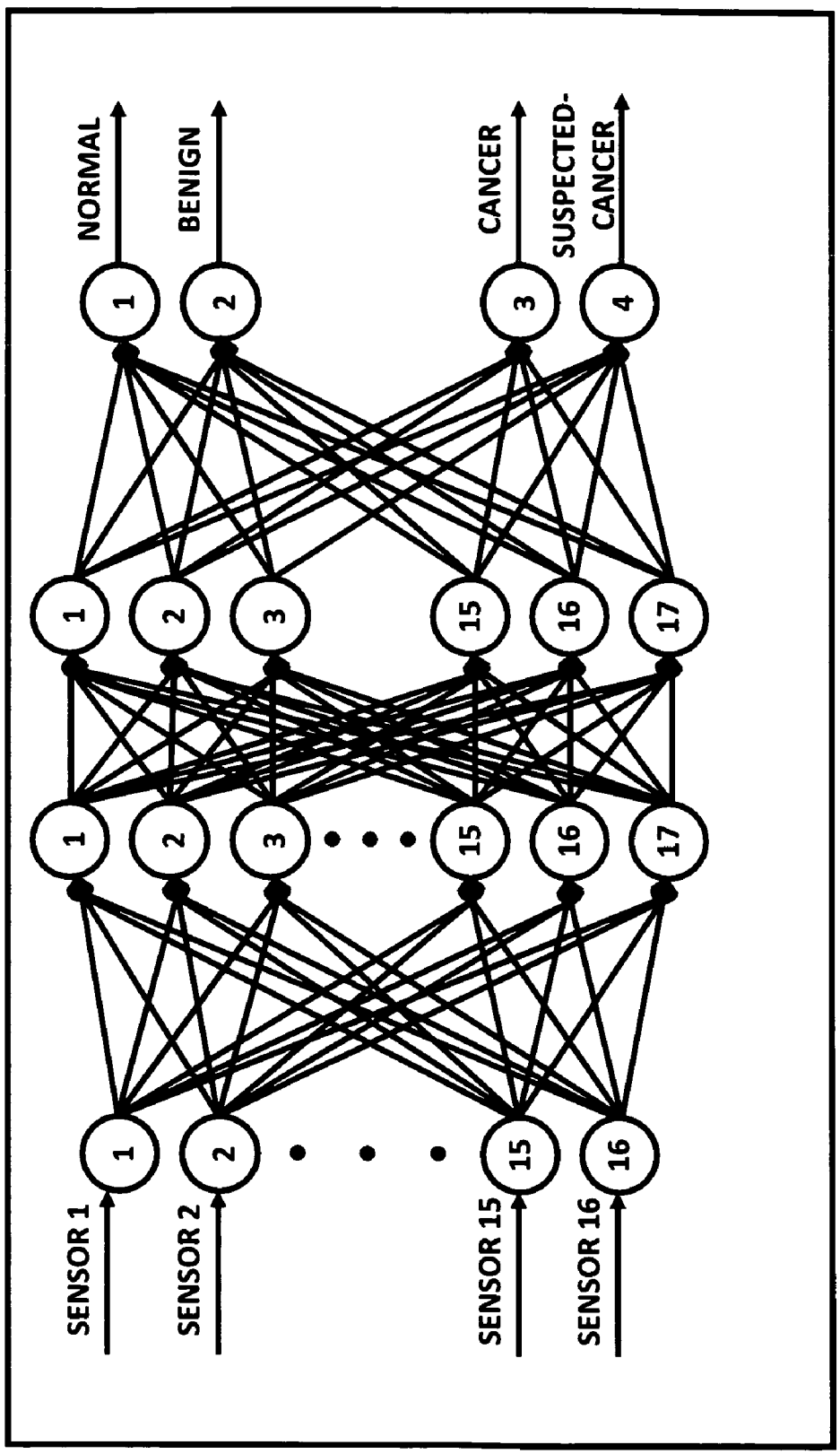
FIG. 5 illustrates a feed-forward neural network in accordance with the preferred embodiment of the present invention.

In the preferred embodiment of the present invention, FIG. 5 depicts a feed-forward neural network used for the classification of the four classes of normal, benign, cancer, and suspected cancer. The feed-forward neural network would be trained using back-propagation. Back propagation was created by generalizing the Widrow-Hoff learning rule to a multiple layer network and nonlinear differentiable transfer function. Input vectors and corresponding target vectors are used to train a network until it can approximate a function, by associating input vectors with specific output vectors, or classify input vectors in an appropriate way. Networks with biases, a sigmoid layer and a linear output layer are capable of approximating any function with a finite number of discontinuities. In an embodiment, a recurrent neural network would be used in place of the feed-forward neural network. In a feed-forward neural network, the output of every node is connected to nodes in the next layer. A recurrent neural network allows for the output of a node to be connected to a node in the next layer, a node in the previous layer, to itself, or to a different node in the current layer. These recurrent connections create an internal state of the network that allows the network to exhibit dynamic temporal behavior, thus allowing the neural network to retain information between observations.

Neural networks typically have one or more hidden layers of sigmoid neurons followed by an output layer of linear neurons. Multiple layers of neurons with nonlinear transfer functions allow the network to learn nonlinear and linear relationships between input and output vectors. The linear output layer allows the network to produce values outside the range −1 to +1.

Before training a neural network, the weight and biases must be initialized. Random numbers around zero were used to initialize weights and biases in the network. The training process requires a set of proper inputs and targets as outputs. During training, the weights and biases of the network are iteratively adjusted to minimize the network performance function. The default performance functions for feed-forward networks are the mean square errors, the average squared errors between the network outputs and the target output.

The weight update aims at maximizing the rate of error reduction. The weight increment is done in small steps; the step size is chosen heuristically, as there is no definite rule for its selection. In the present case, a learning constant η equal to 0.9 (which controls the step size) was chosen by trial and error. While the neural network is presented with a preferred topology, the present invention is not limited to a neural network with such topology. Other neural networks with different topologies, or with recurrent connections, could also be used. The manner in which the neural network, and the other classifier systems, are trained, and any training parameters such as the learning constant, the range of values used to initialize the weights, and the number of iterations needed may all be varied and still be within the scope of the present invention.

An embodiment of the neural network structure or topology is shown in FIG. 5. It consists of 16 input nodes to accept the data from the 16 sensor 112 readings at a point in time, two hidden layers with 17 neurons each, and an output layer with four nodes. The neural network shown in FIG. 5 is fully connected, meaning that every node is connected to every node in the next layer. For example, a node in the input layer would be connected to each of the 17 nodes in the first hidden layer, and each node in the first hidden layer is connected to each of the 17 nodes in the second hidden layer.

The four nodes in the output layer are used to identify the four classes of normal, benign, cancer, and suspected cancer. For example, an output of 0001 could be obtained by having the first output node with a value of 0, the second output node with a value of 0, the third output node with a value of 0, and the fourth output node with a value of 1. The code 0001 could represent that the input temperature readings should be classified as normal. The other three classes could be classified by having an output of 0010 represent benign, an output of 0100 represent cancer, and 1000 represent suspected cancer. Regardless of the type of numeric output used, these output numbers could be converted to a text form or as a label when the diagnosis based on the classification results is presented.

In another embodiment of the present invention, the neural network could consist of a single hidden layer, or the number of nodes on the one or more hidden layers could be equal or less than the number of nodes in the input layer. Further, the neural network does not have to be fully connected. In another embodiment a node would be connected to only half of the nodes in the next layer. Alternatively, the neural network could include recurrent connections, so that the output of a node is not only propagated forward, but also connected back to a node in the previous layer or connected back to a node in the current layer.

Another classifier system that could be used is a radial basis function (RBF) network. RBF networks have a static Gaussian function as the nonlinearity for the hidden layer processing elements. The Gaussian function responds only to a small region of the input space where the Gaussian is centered. The key to a successful implementation of these networks is to find suitable centers for the Gaussian functions. This action can be done with supervised learning, but an unsupervised approach usually produces better results.

The simulation starts with the training of an unsupervised layer. Its function is to derive the Gaussian centers and the widths from the input data. These centers are encoded within the weights of the unsupervised layer using competitive learning. During the unsupervised learning, the widths of the Gaussians are computed based on the centers of their neighbors. The output of this layer is derived from the input data weighted by a Gaussian mixture.

Once the unsupervised layer has completed its training, the supervised segment then sets the centers of Gaussian functions (based on the weights of the unsupervised layer) and determines the width (standard deviation) of each Gaussian. Any supervised topology (such as a multi-layer perceptron) may be used for the classification of the weighted input.

The advantage of the radial basis function network is that it finds the input to the output map using local approximators. Usually the supervised segment is simply a linear combination of the approximators. Since linear combiners have few weights, these networks train extremely fast and require fewer training samples.

A key to classifier systems is their ability to learn nonlinear relationships between the input data and the target data. Nonlinearity is necessary to describe complex phenomena, since a simple linear relationship is not always sufficient to approximate complex systems or sets of data. A linear system is a problem where the variables to be solved for cannot be written as a linear combination of independent components. Most physical systems are nonlinear in nature, hence the need for systems that can learn nonlinear relationships.

Yet another classifier system that could be used is a fuzzy network. In a fuzzy network-based classifier the pattern space is divided into multiple subspaces. For each of these subspaces, the relationships between the target patterns and their classes are described by if-then type fuzzy rules. For example, if temperature readings are above 36 Celsius for 12 consecutive hours, then the class is cancer; or if the temperature readings are above 37 Celsius no more than three times for a period of 12 hours, then the class is normal.

The advantage of this system is that a nonlinear classification boundary can be easily implemented. Unknown patterns are classified by fuzzy inference, and patterns that belong to an unknown class, which is not considered during the training phase, can be easily rejected. A simple learning procedure and a genetic algorithm can be utilized, as is known in the art, to acquire a fuzzy classification system automatically. These methods divide the pattern space into a lattice-like structure. Therefore, many fuzzy rules corresponding to fine subspaces may be necessary to implement a complicated classification boundary.

A fuzzy classifier of the type known in the art could be implemented as follows. The first step is to fuzzify the inputs, in this case the 16 sensor readings at a point in time. The inputs are fuzzified using a symmetric Gaussian membership function given by:

$$f(x; \sigma, \mu) = \frac{e^{-(x-\mu)^2}}{2\sigma^2}$$

where σ and μ are variance and mean respectively. The second step consists of fuzzy inference. Fuzzy inference is the process of formulating the mapping from a given input to an output using fuzzy logic for making decisions. From the fuzzified inputs, the cluster centers are determined using a subtractive clustering method. In the subtractive clustering method, the data point with the highest potential to be the first cluster center is selected. All data points in the vicinity of the first cluster center, as determined by a radius, are removed in order to determine the next data cluster and its center location. This process is iterated until all of the data is within the radius of a cluster center.

The third step is obtaining the membership computation. The final output is obtained using the Sugeno fuzzy model. The output membership function is linear and is given by r=ax+by+cz+d, where a, b, c, d are the adaptive parameters. The output level $r_i$ of each rule is weighted by the firing strength $w_i$ of the rule. The final output of the system is the weighted average of all rule outputs and is computed as:

$$\text{Final Output} = \frac{\sum_{i=1}^{N} w_i r_i}{\sum_{i=1}^{N} w_i}$$

where N is equal to the total number of fuzzy rules.

A Gaussian Mixture Model (GMM) could also be used as a classifier system. A GMM is a parametric model used to estimate a continuous probability density function from a set of multi-dimensional feature observations. It is widely used in data mining, pattern recognition, machine learning and statistical analysis. This Gaussian mixture distribution can be described as a linear superposition of K multidimensional Gaussian components given by:

$$p(x) = \sum_{k=1}^{K} \pi_k N(x | \mu_k, \Sigma_k)$$

where $\pi_k$, $\mu_k$, $\Sigma_k$ are mixing coefficients, mean, and covariance respectively.

The solution for determining the parameters of GMM is estimated by using the maximum likelihood (ML) criterion. A powerful method for maximizing the likelihood solution models is by the general form of Expectation-Maximization (EM) algorithm. To carry out the EM algorithm, first the means, covariances, and mixing coefficients are initialized and the initial value of the log likelihood is evaluated. The E step of the EM algorithm evaluates the responsibilities using the current parameter values as follows:

$$y(z_{nk}) = \frac{\pi_k N(x_n | \mu_k, \Sigma_k)}{\sum_{j=1}^{K} \pi_j N(x_n | \mu_j, \Sigma_j)}$$

The M step of the EM algorithm re-estimates the parameters using the current responsibilities as follows:

$$\mu_k^{new} = \frac{1}{N_k} \sum_{n=1}^{N} y(z_{nk}) x_n$$

$$\Sigma_k^{new} = \frac{1}{N_k} \sum_{n=1}^{N} y(z_{nk})(x_n - \mu_k^{new})(x_n - \mu_k^{new})^T$$

$$\pi_k^{new} = \frac{N_k}{N}$$

where $$N_k = \sum_{n=1}^{N} y(z_{nk})$$

The last step is to evaluate the log likelihood and check for convergence of either the parameters or the log likelihood. If the convergence criterion is not satisfied, then the process returns to the E step and the process repeats. The log likelihood is computed as follows:

$$\ln(p(X \mid \mu, \Sigma, \pi)) = \sum_{n=1}^{N} \ln \left\{ \sum_{k=1}^{K} \pi_k N(x_n \mid \mu_k, \Sigma_k) \right\}$$

The EM algorithm attempts to find the centers of natural clusters in a set of data. The EM algorithm takes more iterations to reach convergence compared with the K-means algorithm, another popular algorithm used in statistics and machine learning for cluster analysis. Hence, it is common to use the K-means algorithm to find the initial estimates of the parameters obtained from a sample of the training data. The K-means algorithm uses the squared Euclidean distance as the measure of dissimilarity between a data point and a prototype vector. This not only limits the type of data variables to be considered but also makes the determination of the cluster means non-robust to outliers. This algorithm starts off by choosing randomly the initial means and assumed unit variances for the diagonal covariance matrix which is being adapted in the present invention.

One of the important attributes of the GMM is its ability to form smooth approximations for any arbitrarily-shaped densities. As real-world data has multi-modal distributions, GMM provides an extremely useful tool to model the characteristics of the data. Another similar property of GMM is the possibility of employing a diagonal covariance matrix instead of a full covariance matrix. Thus, the amount of computational time and complexity can be reduced significantly. GMMs have been widely used in many areas of pattern recognition and classification, with great success in the area of speaker/voice identification and verification.

Yet another classifier system that could be used in the present invention is a support vector machine (SVM). SVMs are known as the "nonparametric" model in which parameters that define the capacity of the model are data-driven in such a way as to match the model capacity to the data complexity. It is developed in reverse order compared to the development of neural networks, as the value of the training error is being fixed and the confidence interval is minimized.

The SVM is a supervised learning method that generates input-output mapping functions from a set of labeled training data. The mapping function can be either a classification function or a regression function. For classification, nonlinear kernel functions are often used to transform input data to a high-dimensional feature space in which the input data become more separable compared to the original input space. Maximum-margin hyper-planes are then created; hence, the model produced depends on only a subset of the training data near the class boundaries. This classification method is currently adopted in the present invention.

The aim of SVM modeling is to find a separating hyperplane which separates positive and negative examples from each other with optimal margin; in other words, the distance of the decision surface and the closest example is maximal. Essentially, this involves orienting the separating hyperplane to be perpendicular to the shortest line separating the convex hulls of the training data for each class, and locating it midway along this line. The vectors that constrain the width of the margin are the support vectors.

Let the separating hyperplane be defined by $x \cdot w + b = 0$ where w is its normal. For linearly separable data labeled $\{x_i, y_i\}$, $x_i \in \mathbb{R}^p$, $y_i \in \{-1, 1\}$, for $i=1, \ldots N$, the optimum boundary chosen with maximal margin criterion is found by minimizing the objective function:

$$E = \|w\|^2$$

subject to $(x_i \cdot w + b)y_i \geq 1$, for all i. \quad (1)

The solution for the optimum boundary $w_0$ is a linear combination of a subset of the training data, $s \in \{1 \ldots N\}$, the support vectors. These support vectors define the margin edges and satisfy the equality $(x_i \cdot w + b)y_s = 1$. Data may be classified by computing the sign of $x \cdot w_0 + b$, with a positive sign denoting a first type of class and a negative sign denoting second type of class.

Generally, the data are not separable, and the inequality in the equation (1) cannot be satisfied. In this case, a "slack" variable $\xi_i$ can be used that represents the amount by which each point is misclassified. The new objective function is now reformulated as $$E = \frac{1}{2}\|w\|^2 + c \sum_i L(\xi_i) \quad (1)$$

subject to $(x_i \cdot w + b)y_i \geq 1 - \xi_i$, for all $i$.

The second term on the right-hand side of equation (2) is the empirical risk associated with those points that are misclassified or lie within the margin. L is a cost function and C is a hyper-parameter that trades-off the effects of minimizing the empirical risk against maximizing the margin. The first term can be thought of as a regularization term, deriving from maximizing the margin, which gives the SVM its ability to generalize well on sparse training data.

Kernel functions can be used to resolve nonlinear boundary problems. Kernel functions define a nonlinear mapping from the input space (observed data) to a manifold in higher dimensional feature space, which is defined implicitly by the kernel functions. The hyperplane is constructed in the feature space and intersects with the manifold, creating a nonlinear boundary in the input space. In practice, the mapping is achieved by replacing the value of the dot products between two vectors in the input space with the value that results when the same dot product is carried out in the feature space. The dot product in the feature space is expressed by functions (i.e., the kernels) of two vectors in input space. The polynomial and radial basis function kernels are commonly used and they are:

$$K(x_i, x_j) = (x_i \cdot x_j + 1)^n$$

and $$K(x_i, x_j) = \exp\left[-\frac{1}{2}\left(\frac{\|x_i - x_j\|}{\sigma}\right)^2\right]$$

Respectively, where n is the order of the polynomial and a is the width of the radial basis function, the dual for the nonlinear case is given by:

$$\alpha^* = \max_\alpha \left( \sum_i \alpha_i + \sum_{i,j} \alpha_i \alpha_j y_i y_j K(x_i \cdot x_j) \right)$$

Subject to $0 \leq \alpha_i \leq C$, $\Sigma_i \alpha_i y_i = 0$. With the above formulation on the use of kernels, an explicit transformation of the data to the feature space is not required. Several algorithms extend the basic binary SVM classifier to a multi-class classifier. Examples consisting of one-against-one SVM, one-against-all SVM, half-against-half SVM, and directed acyclic graph SVM.

In an embodiment of the present invention, the readings at a point in time from all 16 sensors would be stored as a subset of the temperature readings or a line in a file, with the file containing the readings from all sensors for the monitoring period of time. Alternatively, the readings from the 16 sensors can be grouped together using a delimiter, in order to identify the readings from the 16 sensors at different points in time. Abnormalities in temperature readings would be identified by comparing the readings from any two sensors at a point in time. For example, the temperature reading at time T of sensor 1L would be compared to the temperature reading of sensors 2L-8L and 1R-8R. If the difference between the readings of any two sensors is greater than three degrees, or some other threshold value, then the data is marked as an abnormality and ignored for data processing.

A confidential user study was conducted in order to test the preferred embodiment of the present invention. Examinations for each patient were done concurrently on contralateral areas on both breasts under close monitoring for a specific period of time. FIG. 4 illustrates how the sensors were placed on the surface of the breasts of the patients that participated in the user study.

Patient information was collected, compiled, and separately documented to serve as benchmarks for later comparison of the performance of the present invention with the actual diagnosis of the study patients. The information collected included mammogram results, such as suspicion of cancer or benign tumors, the size of the tumor in millimeters; and biopsy results such as ductal carcinoma in-situ, invasive carcinoma, hyperplasia or cysts, among others. Other patient information collected included patient age, status of menopause, etc.

The temperature readings collected from the study participants were classified according to the results of the patients' biopsy results and diagnosis. The data was arranged in two separate files, one file containing data classified as benign and the other file containing data classified as suspect or cancer. These two files were subsequently divided into "easy to detect" and "difficult to detect", based on both the biopsy results and the location of the lesion. The definition for easy to detect was that the sensors 112 line up with the location of the lesion and the biopsy result. The definition for difficult to detect was that the sensors 112 line up with the location of the lesion, but do not match with the biopsy result.

The temperature reading data collected from the study patients was classified according to the results of the patients' illness. The two main categories are namely benign and cancer. These are further divided into easy benign, difficult benign, easy cancer, and difficult cancer.

Due to the need for greater clarity, accuracy and ease of understanding the results from the study, a total of four different classifications were used to assess the collected temperature reading data. The classifications were normal breast, benign lesion, cancerous lesion, and suspected cancer.

A total of 185 patients were evaluated using the present invention. Some of these patients were excluded from the analysis due to incomplete information, such as pending biopsy results and incomplete mammography results or incomplete temperature readings files. After compilation, there were a total of 90 patients involved in the data analysis.

Table 1 shows the data from 90 patients categorized under the four different diagnoses groups.

| Diagnosis | Number of temperature data sets | Number of patients |
| --- | --- | --- |
| Normal | 1500 | 3 |
| Benign | 1500 | 31 |
| Cancer | 1500 | 33 |
| Suspected Cancer | 1500 | 23 |

The 1500 sets of temperature data were randomly selected from different patients belonging to the same group. Each set of the temperature data consisted of sixteen temperature measurements collected concurrently by the sixteen sensors over the test period. There were a total of 6000 sets of temperature readings used. These were further sorted and divided into two groups: 5000 sets to train each of the artificial classifier systems with the number of learning iterations being about one million per classifier, and the remaining 1000 sets were used as test data, to test the performance of the trained classifier systems. It was necessary to have more training data than testing data to allow for better training of the classifier systems.

Figure 6:
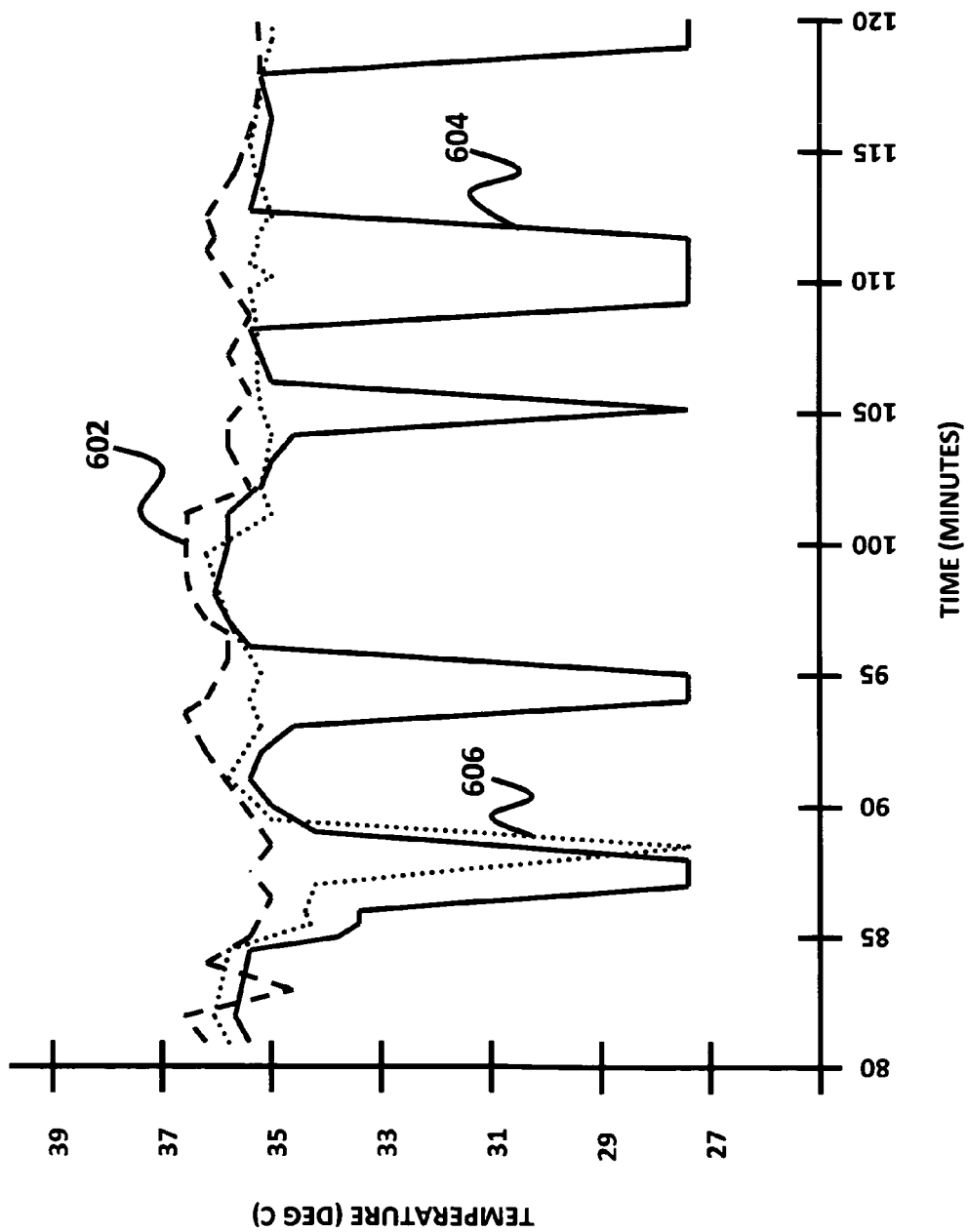
FIG. 6 illustrates temperature readings for three sensors plotted versus time, showing abnormal temperature readings.

Data inspections were required to ensure that temperature readings were clean of all extraneous noise and abnormalities. Inspection was done through graphical analyses by converting all the sets of temperature readings from each patient into line plots or line charts. For each patient, the temperature from each of the sixteen sensors was plotted on the same graph, with each sensor denoted by a different color. If any abnormalities were found, such as great fluctuations of the temperature on a particular sensor, the patient's data would be excluded from the analysis. Examples of such abnormalities are illustrated in FIG. 6. The three lines 602, 604 and 606 on FIG. 6 represent the temperature readings received during the various time for three out of 16 sensors. The temperature readings are expected to vary within a reasonable range. This is the case for line 602 representing one sensor from the graph on FIG. 6, which remained relatively level. The other two lines, 604 and 606, represent two sensors that show drastic drops in temperatures from one time period to the next. The potential causes for such phenomena include poor contact between the sensors and the breast surface, continuous data recording after the screening system has shut off, and sensors dropped off from the breast surface in the midst of temperature recording.

There are several ways to address such temperature abnormalities during data collection. In one embodiment of the present invention, the temperature reading data that has the lowest temperature is manually removed by the subject during the data collection phase. In yet another embodiment, an alarm would be placed on each sensor to detect abnormality during monitoring and data collection. The alarm could then discard the data without even storing it. Alternatively, the alarm could trigger a visual or an audial cue that informs the subject to readjust the troubled sensor or sensors. In an alternative embodiment, all of the data would be collected, but the data would go through a data cleaning process before data analysis. The data cleaning process would identify temperatures that are outside of a reasonable range and would subsequently delete the corresponding data. A statistical analysis could be used for the data cleaning, with outlier temperature readings being deleted. Yet another solution would be to apply a regression approach to select the best appropriate input data for the training and testing of the classifier systems.

A key aspect of the present invention is normalization of the temperature readings. Each set of temperature readings has its own temperature range, depending on each individual's health and body conditions. For example, some patients could have body temperature ranges from 30 to 35 Celsius, while others could range from 32 to 36 Celsius. In addition, temperature ranges could vary for a particular patient at different times of the day. Further, the temperature of one breast could normally be different from the temperature of the other breast.

The classifier systems are trained by presenting the training data over several iterations. The number of iterations can be a fixed number, such as 1000 iterations, or it can depend on the classifier system reaching an acceptable level of performance, such as classifying data correctly with at least 80% accuracy. The system used for the user study was sufficiently trained after about 5000 iterations.

Five classifiers were tested during the user study: a feed-forward neural network trained with back-propagation (BPA), a radial basis function, a fuzzy network, a Gaussian mixture model (GMM), and a support vector machine (SVM). In testing the five classifiers, at least 1000 sets of test data were used to compare the performance of the classifiers. The following table shows the performance of the five classifiers used for classification.

| Type of classifiers | No. of training data used | No. of testing data used | Percentage of correct classification |
| --- | --- | --- | --- |
| BPA | 5000 | 1000 | 83.1 |
| RBF | 5000 | 1000 | 86.1 |
| Fuzzy | 5000 | 1000 | 77.4 |
| GMM | 5000 | 1000 | 90.6 |
| SVM | 5000 | 1000 | 85.6 |
| AVERAGE | | | 84.5 |

All five classifiers managed to obtain approximately 85% of correct classification. BPA classifier was trained using 2 hidden layers of 17 neurons each. As noted above, FIG. 5 shows such a neural network with four layers.

The BPA classifier was only able to classify the unknown data correctly with an accuracy of 83.1%. Among these five classifiers, GMM had the best performance, as it had obtained the highest percentage of correct classification of 90.6%, whereas RBF, Fuzzy, and SVM obtained 86.1%, 77.4%, and 85.6% of accuracy respectively. The performance of the five classifiers was evaluated using three performance indices of sensitivity, specificity, and positive predictive value.

Sensitivity of a test is the proportion of people with the disease who have a positive test result, the higher the sensitivity, the greater the detection rate and the lower the false negative (FN) rate. The specificity of the test is the proportion of people without the disease who have a negative test result, the higher the specificity, the lower the false positive rate and the lower the proportion of people who have the disease who will be unnecessarily worried or exposed to unnecessary treatment. The positive predictive value (PPV) of a test is the probability of a patient with a positive test actually having a disease.

The ROC curve is a plot of sensitivity against (1-specificity). Sensitivity, also known as true positive fraction (TFP), refers to the probability that a test result was positive when the disease was present. The area under the ROC curve indicates the performance of the classifier across the entire range of cut-off points. Conventionally, the area under the ROC curve must range between 0.5 and 1. If the area was closer to 1, this would show that the classifier had better accuracy in the testing. Currently, the area under the ROC curve is the best indicator for the classifier's performance with regard to the misclassification rate and the measure of risk based on confusion and loss matrices. This is because ROC was able to provide the most complete way of quantifying the diagnostic accuracy.

The ROC results based on the sensitivity, specificity, positive predictive value and area under the curve for the three classifiers were tabulated in the following table.

| Classifier | TN | TP | FP | FN | Sensitivity | Specificity | Area under the curve | +PV |
| --- | --- | --- | --- | --- | --- | --- | --- | --- |
| BPA | 209 | 622 | 41 | 128 | 82.9 | 83.6 | 0.833 | 93.8 |
| RBF | 195 | 666 | 55 | 84 | 88.8 | 78 | 0.834 | 92.4 |
| Fuzzy | 189 | 585 | 61 | 165 | 78 | 75.6 | 0.768 | 90.6 |
| GMM | 195 | 711 | 55 | 39 | 94.8 | 78 | 0.864 | 92.8 |
| SVM | 226 | 630 | 24 | 120 | 84 | 90.4 | 0.872 | 96.3 |

The results obtained from the 1000 testing data were classified under true negative (TN), true positive (TP), false positive (FP) and false negative (FN), depending on each classifier's situation. As shown in the table, the GMM classifier showed the highest sensitivity of 94.8% among the five classifiers. This was followed by RBF and SVM with sensitivity of 88.8% and 84% respectively. This observation had showed that the higher sensitivity of the classifier would result in a greater detection rate by causing the false negative rate to be lower.

SVM showed the highest specificity of 90.4%, and this was justified by the number of true negative cases. This result was followed by BPA with specificity of 83.6%, and both GMM and RBF had the same specificity of 78%. Fuzzy showed the least specificity of 75.6%. In tabulating the positive predictive value, SVM classifier showed the highest value of 96.3, followed by BPA with value of 93.8. The PPV values for GMM, RBF and Fuzzy were 92.8, 92.4, and 90.6 respectively.

The area under the curve is also an important parameter as it determines the overall classification accuracy for the five classifiers. The ROC curves for each of the five classifiers were plotted and compared. The SVM had the largest area under the curve, whereas the Fuzzy classifier had the smallest area among the five classifiers. This result was reinforced based on the area under the curve tabulated in the previous table. It was accountable for SVM to have an area of 0.872 which is the largest area under the curve as compared to the other four classifiers with an area of 0.768, 0.833, 0.834 and 0.864 (Fuzzy, BPA, RBF, and GMM), respectively. As seen from the results obtained, SVM was the most accurate classifier due to its area under the ROC curve being closer to 1.

In the statistic analysis of ROC curves, SVM was considered the outstanding classifier, even though GMM had achieved the highest sensitivity. This result was based on the four performance indices in which SVM had attained the best result in three of these indices. SVM had the greatest specificity and positive predictive value and had also attained the largest area under the curve which implies its accuracy. Therefore, SVM was considered to be an excellent classifier.

Figure 7:
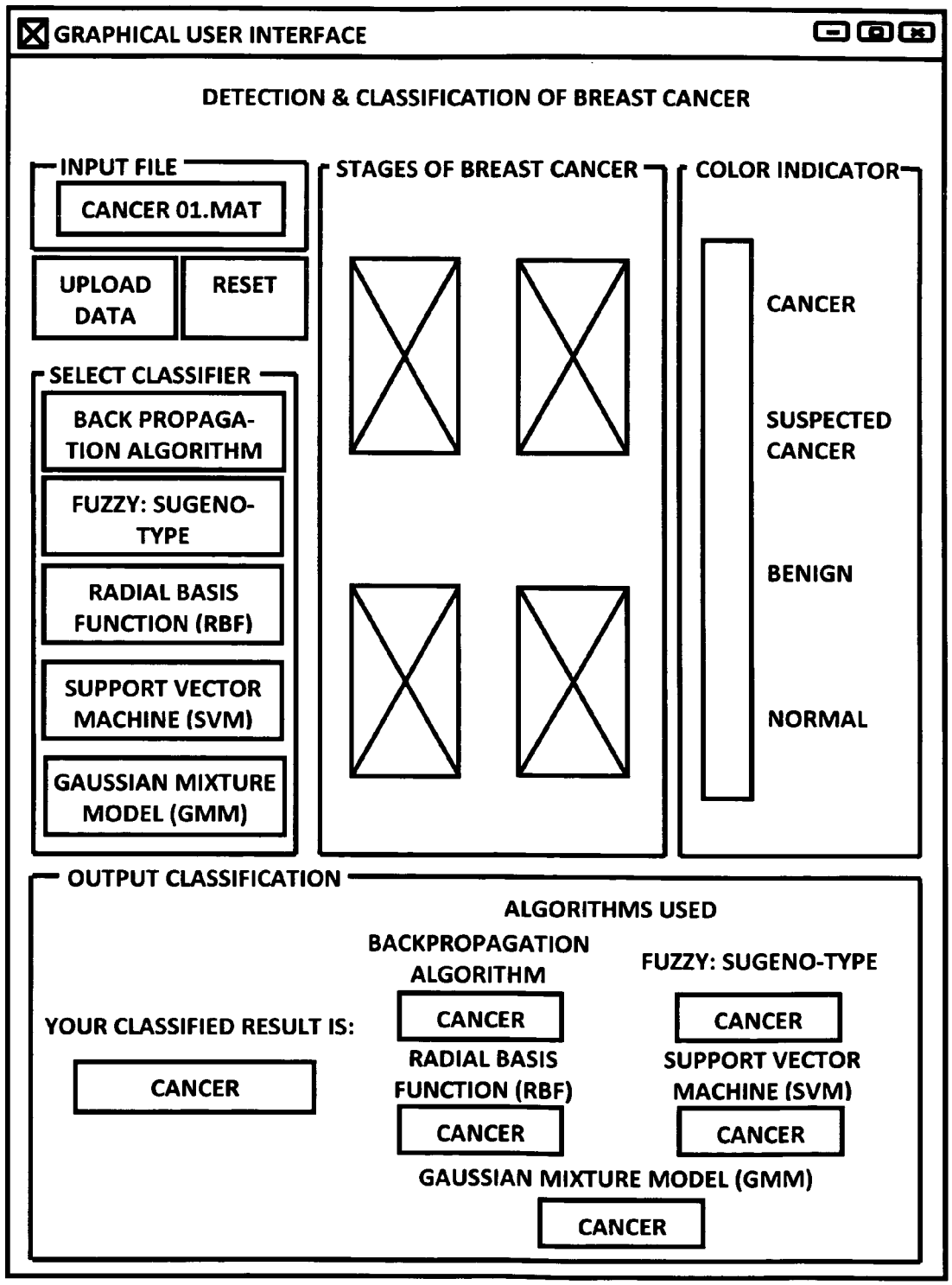
FIG. 7 illustrates a user interface for the temperature readings analysis and diagnosis in accordance with the preferred embodiment of the present invention.

FIG. 7 illustrates the graphical user interface in accordance with an embodiment of the present invention for the detection and classification of breast cancer. The procedures for the interface were carried out by uploading the set of temperature data required to be classified. This action was done by clicking on the push button labeled "Upload Data." Once the data has been selected, the file name will appear on the "Input" text box. The user may then select any of the five classifiers which they wish to test, for instance back-propagation, or GMM, etc. The various stages of breast cancer are represented by the four different images (illustrated as an "X" in FIG. 7 for purposes of simplifying the illustration), namely: normal, benign, cancer, and suspected-cancer. In an embodiment, a color indicator would also be used to identify the various stages of the breast cancer.

The classified result will be shown in the output classification section. For instance, if the classified result is "Cancer," the box next to it will turn pink which represents "Cancer" as shown in the color indicator. The image which represents "Cancer" will also be highlighted in the stages of breast cancer. Under the output classification, the results obtained by the other algorithms are also displayed. The classified result will be based on the result from the majority of the algorithms. For instance, if the result shown for most of the algorithms is "Cancer," then the classified result will be shown as "Cancer." Lastly, the whole procedure can be repeated by clicking on the push button "Reset" in order to use another classifier or to input new data.

The present invention reveals that the use of temperature as a tool to detect breast cancer is possible, though the performance of the current discrete temperature approach will improve the addition of further training data, since all of these classifiers are iterative and improve in their accuracy as more data is added, especially for much younger females who are not suitable for mammograms.

The interpretive system of the present invention incorporates dynamic thermal analysis for the detection of breast cancer. In a preferred embodiment, five classifiers (neural network trained with back-propagation, radial basis function, fuzzy networks, Gaussian mixture model, and support vector machines) are used for decision making. The accuracy of these classifiers depends on the size and quality of the training data, the rigor of the training imparted and also the parameters used to represent the input, consisting of the breast surface temperature. With more temperature data being analyzed, the five classifiers were able to achieve more than 90% of accuracy in classifying the four different diagnoses (normal, benign, cancer, and suspected-cancer). A significant advantage of the classifiers is that the system provides a detection system without human interpretation or human error. By using five separate methods of analyzing data from five independent classifiers, it was possible to generate positive predictive values that provide a picture of the underlying physiology of the breast without requiring human interpretation of images.

While the present invention has been illustrated and described herein in terms of a preferred embodiment and several alternatives, it is to be understood that the techniques described herein can have a multitude of additional uses and applications. Accordingly, the invention should not be limited to just the particular description and various drawing figures contained in this specification that merely illustrate a preferred embodiment and application of the principles of the invention.

What is claimed is:

1. A system for analyzing a set of temperature readings of breast tissue of a subject to identify suspect tissue and non-suspect tissue, comprising:
   a set of temperature sensors for sensing the set of temperature readings over a predetermined period, each temperature sensor among the set of temperature sensors placed at a predetermined position on a breast of the subject;
   a storage system storing the set of temperature readings received from the set of temperature sensors; and
   an ensemble of classifier systems including two or more classifier systems, the ensemble of classifier systems trained using one or more actual temperature readings including an above average temperature reading corresponding to suspect tissue, an average temperature reading corresponding to non-suspect tissue, and an anomalous temperature reading corresponding to non-suspect tissue, the ensemble of classifier systems receiving the set of temperature readings as an input, generating two or more output labels identifying the breast tissue as suspect tissue or non-suspect tissue, and combining the two or more output labels into a single diagnosis identifying the breast tissue as suspect tissue or non-suspect tissue, wherein a weight of each label from the two or more output labels determines a relative contribution of the label towards the single diagnosis.

2. The system as recited in claim 1, wherein suspect tissue includes cancerous tissue, benign tissue, and suspected cancerous tissue.

3. The system as recited in claim 1, wherein the ensemble of classifier systems is trained using the one or more actual temperature readings corresponding to one or more known output labels using one or more of supervised learning, unsupervised learning, or reinforcement learning.

4. The system as recited in claim 1, wherein the ensemble of classifier systems includes a neural network.

5. The system as recited in claim 4, wherein the neural network was trained using one or more actual temperature readings corresponding to one or more known output labels using either back-propagation or neuroevolution.

6. The system as recited in claim 1, wherein the ensemble of classifier systems includes two or more neural networks, each neural network among the two or more neural networks provided with different node weights, a different topology, or different activation functions or trained using a different set of one or more actual temperature readings corresponding to one or more known output labels.

7. The system as recited in claim 1, wherein the ensemble of classifier systems includes one or more of a back-propagation neural network, a neural network trained with neuroevolution, a radial basis function, a Gaussian mixture model, a fuzzy network, a neural network, and a support vector machine.

8. The system as recited in claim 1, wherein the predetermined period is 24 hours or less.

9. The system as recited in claim 1, further comprising a portable device including a microprocessor, the storage system contained within the portable device and controlled by the microprocessor, each temperature sensor connected to the portable device by a lead among a set of leads.

10. The system as recited in claim 9, wherein each lead is color coded based on the predetermined position where the temperature sensor will be placed on the breast.

11. The system as recited in claim 10, wherein each temperature sensor is labeled based on the predetermined position where the temperature sensor will be placed on the breast.

12. The system as recited in claim 9, wherein the set of temperature sensors are divided into a first group and a second group, each of the temperature sensors in the first group of temperature sensors being placed in the predetermined position on a left breast of the subject and each of the temperature sensors in the second group of temperature sensors being placed in the predetermined position on a right breast of the subject.

13. The system as recited in claim 1, wherein the set of temperature sensors are divided into a first group and a second group, one temperature sensor from the first group placed below a nipple of a left breast of the subject and one temperature sensor from the second group placed below a nipple of a right breast of the subject, one temperature sensor from the first group placed in an upper outer quadrant of the left breast and one temperature sensor from the second group placed in an upper outer quadrant of the right breast, one temperature sensor from the first group placed in an upper outer quadrant toward axilla associated with the left breast and one temperature sensor from the second group placed in an upper outer quadrant toward axilla associated with the right breast, one temperature sensor from the first group placed on an upper areola of the left breast and one temperature sensor from the second group placed on an upper areola of the right breast, one temperature sensor from the first group placed on a vertical midline above a horizontal midline of the left breast and one temperature sensor from the second group placed on a vertical midline above a horizontal midline of the right breast, one temperature sensor from the first group placed in an upper inner quadrant of the left breast and one temperature sensor from the second group placed in an upper inner quadrant of the right breast, one temperature sensor from the first group placed in an ambient temperature zone of the left breast and one temperature sensor from the second group placed in an ambient temperature zone of the right breast, and one temperature sensor from the first group placed in a flexible position of the left breast and one temperature sensor from the second group placed in a flexible position of the right breast.

14. The system as recited in claim 13, wherein the flexible position of the left breast and the flexible position of the right breast includes in an area of concern, near a palpable lesion, and in a contralateral position.

15. The system as recited in claim 1, further comprising a substantially lobate shaped sensor placeholder with a set of four appendages, each appendage among the four appendages forming a series of holes within each appendage, each hole among the series of holes serving as a location for placing one of the temperature sensors among the set of temperature sensors, and wherein a central area of the sensor placeholder forms a center hole for placement over a nipple of the breast to align the sensor placeholder.

16. The system as recited in claim 15, wherein the sensor placeholder is aligned on the breast with three of the four appendages positioned above the nipple.

17. The system as recited in claim 16, wherein a first sensor placeholder is aligned over a left breast and a second sensor placeholder is aligned over a right breast of the subject, wherein the set of temperature sensors are divided into a first group and a second group, one temperature sensor from the first group placed within a hole of a first appendage of the first sensor placeholder and below a nipple of the left breast and one temperature sensor from the second group placed within a hole of a first appendage of the second sensor placeholder and below a nipple of the right breast, one temperature sensor from the first group placed within a hole of a second appendage of the first sensor placeholder and in an upper outer quadrant of the left breast and one temperature sensor from the second group placed within a hole of a second appendage of the second placeholder and in an upper outer quadrant of the right breast, one temperature sensor from the first group placed within a second hole of a second appendage of the first sensor placeholder and in an upper outer quadrant toward axilla associated with the left breast and one temperature sensor from the second group placed within a second hole of a second appendage of the second sensor placeholder and in an upper outer quadrant toward axilla associated with the right breast, one temperature sensor from the first group placed within a hole of a third appendage of the first sensor placeholder and on an upper areola of the left breast and one temperature sensor from the second group placed within a hole of a third appendage of the second sensor placeholder and on an upper areola of the right breast, one temperature sensor from the first group placed within a second hole of a third appendage of the first sensor placeholder and on a vertical midline above a horizontal midline of the left breast and one temperature sensor from the second group placed within a second hole of a third appendage of the second sensor placeholder and on a vertical midline above a horizontal midline of the right breast, one temperature sensor from the first group placed within a hole of a fourth appendage of the first sensor placeholder and in an upper inner quadrant of the left breast and one temperature sensor from the second group placed within a hole of a fourth appendage of the second sensor placeholder and in an upper inner quadrant of the right breast, one temperature sensor from the first group placed within a hole of the set of four appendages of the first sensor placeholder and in an ambient temperature zone of the left breast and one temperature sensor from the second group placed within a hole of the set of four appendages of the second sensor placeholder and in an ambient temperature zone of the right breast, and one temperature sensor from the first group placed within a hole of the set of four appendages of the first sensor placeholder and in a flexible position of the left breast and one temperature sensor from the second group placed within a hole of the set of four appendages of the second sensor placeholder and in a flexible position of the right breast.

18. The system as recited in claim 1, wherein the set of temperature sensors is located on the subject, wherein the storage system and the ensemble of classifier systems is located in a remote location, further comprising a wireless transmitter transmitting the set of temperature readings to the storage system.

19. The system as recited in claim 1, wherein the set of temperature sensors and the storage system are located on the subject, further comprising a second storage system located in a remote location, the second storage system receiving the set of temperature readings from the storage system, and wherein the ensemble of classifier systems receives the set of temperature readings from the second storage system.

20. The system as recited in claim 1, wherein the ensemble of classifier systems is located in a remote location.

21. The system as recited in claim 1, further comprising a computer operating the ensemble of classifier systems, the computer including a user interface enabling a user of the computer to control operation of the ensemble of classifier systems and providing the user with a visual indication of the two or more output labels and the single diagnosis.

22. The system as recited in claim 21, wherein the user interface further provides a visual indication of a stage of breast cancer for the breast tissue identified as suspect tissue.

23. The system as recited in claim 21, wherein the visual indication includes a color indication.

24. The system as recited in claim 23, wherein the visual indication further includes a word indication.

25. A system for analyzing a set of temperature readings of breast tissue of a subject to identify suspect tissue and non-suspect tissue, comprising:
a set of temperature sensors for sensing the set of temperature readings over a predetermined period, each temperature sensor among the set of temperature sensors placed at a predetermined position on a breast of the subject; and
an ensemble of classifier systems including two or more classifier systems, the ensemble of classifier systems trained using one or more actual temperature readings including an above average temperature reading corresponding to suspect tissue, an average temperature reading corresponding to non-suspect tissue, and an anomalous temperature reading corresponding to non-suspect tissue, the ensemble of classifier systems receiving the set of temperature readings as an input, generating two or more output labels identifying the breast tissue as suspect tissue or non-suspect tissue, and combining the two or more output labels into a single diagnosis identifying the breast tissue as suspect tissue or non-suspect tissue, wherein a weight of each label from the two or more output labels determines a relative contribution of the label towards the single diagnosis.

26. The system as recited in claim 25, wherein suspect tissue includes cancerous tissue, benign tissue, and suspected cancerous tissue.

27. The system as recited in claim 25, wherein the ensemble of classifier systems includes a neural network.

28. The system as recited in claim 25, wherein the ensemble of classifier systems includes two or more neural networks, each neural network among the two or more neural networks provided with different node weights, a different topology, or different activation functions or trained using a different set of one or more actual temperature readings corresponding to one or more known output labels.

29. The system as recited in claim 25, wherein the ensemble of classifier systems includes one or more of a back-propagation neural network, a neural network trained with neuroevolution, a radial basis function, a Gaussian mixture model, a fuzzy network, a neural network, and a support vector machine.

30. The system as recited in claim 25, wherein the predetermined period is 24 hours or less.

31. The system as recited in claim 25, wherein the set of temperature sensors are divided into a first group and a second group, each of the temperature sensors in the first group of temperature sensors being placed in the predetermined position on a left breast of the subject and each of the temperature sensors in the second group of temperature sensors being placed in the predetermined position on a right breast of the subject.

32. The system as recited in claim 25, wherein the set of temperature sensors are divided into a first group and a second group, one temperature sensor from the first group placed below a nipple of a left breast of the subject and one temperature sensor from the second group placed below a nipple of a right breast of the subject, one temperature sensor from the first group placed in an upper outer quadrant of the left breast and one temperature sensor from the second group placed in an upper outer quadrant of the right breast, one temperature sensor from the first group placed in an upper outer quadrant toward axilla associated with the left breast and one temperature sensor from the second group placed in an upper outer quadrant toward axilla associated with the right breast, one temperature sensor from the first group placed on an upper areola of the left breast and one temperature sensor from the second group placed on an upper areola of the right breast, one temperature sensor from the first group placed on a vertical midline above a horizontal midline of the left breast and one temperature sensor from the second group placed on a vertical midline above a horizontal midline of the right breast, one temperature sensor from the first group placed in an upper inner quadrant of the left breast and one temperature sensor from the second group placed in an upper inner quadrant of the right breast, one temperature sensor from the first group placed in an ambient temperature zone of the left breast and one temperature sensor from the second group placed in an ambient temperature zone of the right breast, and one temperature sensor from the first group placed in a flexible position of the left breast and one temperature sensor from the second group placed in a flexible position of the right breast.

33. The system as recited in claim 32, wherein the flexible position of the left breast and the flexible position of the right breast includes in an area of concern, near a palpable lesion, and in a contralateral position.

34. The system as recited in claim 25, further comprising a substantially lobate shaped sensor placeholder with a set of four appendages, each appendage among the four appendages forming a series of holes within each appendage, each hole among the series of holes serving as a location for placing one of the temperature sensors among the set of temperature sensors, and wherein a central area of the sensor placeholder forms a center hole for placement over a nipple of the breast to align the sensor placeholder.

35. The system as recited in claim 34, wherein the sensor placeholder is aligned on the breast with three of the four appendages positioned above the nipple.

36. The system as recited in claim 35, wherein a first sensor placeholder is aligned over a left breast and a second sensor placeholder is aligned over a right breast of the subject, wherein the set of temperature sensors are divided into a first group and a second group, one temperature sensor from the first group placed within a hole of a first appendage of the first sensor placeholder and below a nipple of the left breast and one temperature sensor from the second group placed within a hole of a first appendage of the second sensor placeholder and below a nipple of the right breast, one temperature sensor from the first group placed within a hole of a second appendage of the first sensor placeholder and in an upper outer quadrant of the left breast and one temperature sensor from the second group placed within a hole of a second appendage of the second placeholder and in an upper outer quadrant of the right breast, one temperature sensor from the first group placed within a second hole of a second appendage of the first sensor placeholder and in an upper outer quadrant toward axilla associated with the left breast and one temperature sensor from the second group placed within a second hole of a second appendage of the second sensor placeholder and in an upper outer quadrant toward axilla associated with the right breast, one temperature sensor from the first group placed within a hole of a third appendage of the first sensor placeholder and on an upper areola of the left breast and one temperature sensor from the second group placed within a hole of a third appendage of the second sensor placeholder and on an upper areola of the right breast, one temperature sensor from the first group placed within a second hole of a third appendage of the first sensor placeholder and on a vertical midline above a horizontal midline of the left breast and one temperature sensor from the second group placed within a second hole of a third appendage of the second sensor placeholder and on a vertical midline above a horizontal midline of the right breast, one temperature sensor from the first group placed within a hole of a fourth appendage of the first sensor placeholder and in an upper inner quadrant of the left breast and one temperature sensor from the second group placed within a hole of a fourth appendage of the second sensor placeholder and in an upper inner quadrant of the right breast, one temperature sensor from the first group placed within a hole of the set of four appendages of the first sensor placeholder and in an ambient temperature zone of the left breast and one temperature sensor from the second group placed within a hole of the set of four appendages of the second sensor placeholder and in an ambient temperature zone of the right breast, and one temperature sensor from the first group placed within a hole of the set of four appendages of the first sensor placeholder and in a flexible position of the left breast and one temperature sensor from the second group placed within a hole of the set of four appendages of the second sensor placeholder and in a flexible position of the right breast.

37. The system as recited in claim 25, wherein the set of temperature sensors is located on the subject, wherein the ensemble of classifier systems is located in a remote location, further comprising a wireless transmitter transmitting the set of temperature readings to the ensemble of classifier systems.

38. The system as recited in claim 25, wherein the ensemble of classifier systems is located in a remote location.

39. The system as recited in claim 25, further comprising a computer operating the ensemble of classifier systems, the computer including a user interface enabling a user of the computer to control operation of the ensemble of classifier systems and providing the user with a visual indication of the two or more output labels and the single diagnosis.

40. The system as recited in claim 39, wherein the user interface further provides a visual indication of a stage of breast cancer for the breast tissue identified as suspect tissue.

41. The system as recited in claim 39, wherein the visual indication includes a color indication.

42. The system as recited in claim 41, wherein the visual indication further includes a word indication.

43. A system for analyzing a set of temperature readings of breast tissue of a subject to identify suspect tissue and non-suspect tissue, comprising:
- a storage system storing the set of temperature readings, the set of temperature readings gathered over a predetermined period from a set of temperature sensors placed at a predetermined position on a breast of the subject; and
- an ensemble of classifier systems including two or more classifier systems, the ensemble of classifier systems trained using one or more actual temperature readings including an above average temperature reading corresponding to suspect tissue, an average temperature reading corresponding to non-suspect tissue, and an anomalous temperature reading corresponding to non-suspect tissue, the ensemble of classifier systems receiving the set of temperature readings as an input, generating two or more output labels identifying the breast tissue as suspect tissue or non-suspect tissue, and combining the two or more output labels into a single diagnosis identifying the breast tissue as suspect tissue or non-suspect tissue, wherein a weight of each label from the two or more output labels determines a relative contribution of the label towards the single diagnosis.

* * * * *